(12) United States Patent
Spurge

(10) Patent No.: US 9,107,811 B2
(45) Date of Patent: *Aug. 18, 2015

(54) COMPOSITION FOR TREATING SKIN LESIONS

(75) Inventor: John Spurge, Mareeba (AU)

(73) Assignee: Sci-Chem International PTY. LTD., Prestons (AU)

(*) Notice: Subject to any disclaimer, the term of this patent is extended or adjusted under 35 U.S.C. 154(b) by 1770 days.

This patent is subject to a terminal disclaimer.

(21) Appl. No.: 11/993,236

(22) PCT Filed: Jun. 20, 2006

(86) PCT No.: PCT/AU2006/000863
§ 371 (c)(1),
(2), (4) Date: May 6, 2008

(87) PCT Pub. No.: WO2006/135965
PCT Pub. Date: Dec. 28, 2006

(65) Prior Publication Data
US 2010/0278936 A1    Nov. 4, 2010

(30) Foreign Application Priority Data

Jun. 20, 2005  (AU) ................................ 2005903229

(51) Int. Cl.
 A61K 33/34   (2006.01)
 A61K 36/38   (2006.01)
 A61K 36/886  (2006.01)
 A61K 9/00    (2006.01)

(52) U.S. Cl.
 CPC ............... *A61K 9/0014* (2013.01); *A61K 33/34* (2013.01); *A61K 36/38* (2013.01); *A61K 36/886* (2013.01)

(58) Field of Classification Search
 CPC ... A61K 9/0014; A61K 36/886; A61K 33/34; A61K 36/38
 USPC .......... 424/638, 616, 630, 730, 744; 514/499, 514/500
 See application file for complete search history.

(56) References Cited

U.S. PATENT DOCUMENTS

| | | |
|---|---|---|
| 4,898,891 A | 2/1990 | Lavie et al. |
| 5,514,667 A | 5/1996 | Cullis-Hill |
| 5,698,184 A | 12/1997 | Pickart |
| 6,291,241 B1 | 9/2001 | Castor et al. |
| 6,699,512 B2* | 3/2004 | Quintanilla Almagro et al. ............................ 424/730 |
| 2003/0077938 A1 | 4/2003 | Yi-Tse |
| 2003/0104043 A1 | 6/2003 | Brown et al. |
| 2004/0137088 A1 | 7/2004 | Koch et al. |
| 2004/0185123 A1 | 9/2004 | Mazzio et al. |
| 2004/0191330 A1* | 9/2004 | Keefe et al. .................... 424/638 |
| 2005/0100563 A1 | 5/2005 | Hexamer |
| 2006/0067959 A1 | 3/2006 | Nimni et al. |
| 2006/0089342 A1* | 4/2006 | Gavin et al. .................... 514/184 |
| 2011/0064826 A1 | 3/2011 | Spurge |

FOREIGN PATENT DOCUMENTS

| | | |
|---|---|---|
| DE | 19853998 A1 * | 5/2000 |
| EP | 0046409 | 2/1982 |
| GB | 1493750 | 11/1977 |
| JP | H01-216922 | 8/1989 |
| WO | 94/27594 | 12/1994 |
| WO | 97/44047 | 11/1997 |
| WO | WO 97/44047 | 11/1997 |
| WO | WO02051427 | 7/2002 |
| WO | WO2006096937 | 9/2006 |

OTHER PUBLICATIONS

Choraphor: Frequently Asked Questions Datasheet [online]. Choraphor, 2004 [retrieved on Aug. 15, 2011]. Retrieved from the Internet: <URL:http://web.archive.org/web/20040603073428/http://choraphorcom/faq.htm, pp. 1-11.*
Skin Lesion. [online]. Better Medicine, 2011 [retrieved on Aug. 15, 2011]. Retrieved from the Internet: <URL:http://www.bettermedicine.com/article/skin-lesion, pp. 1-2.*
Offen. DE 19853998, EPO Machine Translation, pp. 1-2. added Feb. 8, 2015 May 2000.*
Sagripanti, J., Virus Inactivation of Copper or Iron Ions Alone and in the Presence of Peroxide, 1993, Applied and Environmental Microbiology, vol. 59, No. 12, pp. 4374-4376.*
Uses of Copper Compounds, CDA Technical Note TN11, Copper Development Association, 1972, pp. 1-22.*
Using Preservatives to Extend the Shelf Life of Your Products. [online], 2004, [retrieved on Aug. 16, 2011]. Retrieved from the Internet:URL: http://web.archive.org/web/20041116084020/http://www.fromnaturewithlove.com/library/preservatives.asp, pp. 1-5.*
Aviralex, www.aviralex.com/faq.htm, accessed May 18, 2010.
Betanzos+Cabrera, Inactivation of HSV-2 by ascorbate-Cu(II) and its protecting evaluation in CF-1 mice against encephalitis., J Virol Methods. Sep. 15, 2004;120(2):161-5.
Choraphor, http://www.choraphor.com/herpes-facts.htm, Choraphor—"Frequently asked questions", accessed May 18, 2010.
Sagripanti, et al., Mechanism of copper-mediated inactivation of herpes simplex virus., Antimicrob Agents Chemother. Apr. 1997; 41(4): 812-817.
Schempp, et al. Topical application of St John's wort (*Hypericum perforatum* L.) and of its metabolite hyperforin inhibits the allostimulatory capacity of epidermal cells., British Journal of Dermatology—May 2000; 142(5): 979-984.
Vogler, et al., Aloe vera: a systematic review of its clinical effectiveness., Br J Gen Pract. Oct. 1999; 49(447): 823-828.

(Continued)

*Primary Examiner* — Sue Liu
*Assistant Examiner* — Andriae M Holt
(74) *Attorney, Agent, or Firm* — Carol L. Francis; Rudy J. Ng; Bozicevic, Field & Francis LLP

(57) ABSTRACT

The present invention provides a composition for topical treatment of skin and mucosal membrane lesions comprising a synergistic combination of copper compound and hypericum perforatum extract.

24 Claims, No Drawings

(56) References Cited

OTHER PUBLICATIONS

Mohammad Azam Khan et al., "Key Attributes of TKDL", Muheet-e-Azam, vol. III, 1887, Matba Nizami, Kanpur.
Madanapala et al., "Key Attributes of TKDL", Madanapalanighantauh, translated by Rama Prasad, 1998, Khemaraj Shri Krishnadas Prakashan, Bombay.
Mohammad Najmul Ghani Khan et al., "Key Attributes of TKDL", Khazaain-al-Advia, vol. I, 1911, Nadeem Yunus Printer / Sheikh Mohd Basheer & Sons, Lahore.
Kannusamy Pillai et al., "Key Attributes of TKDL", Chikithsa Rathna Deepam, 1956, Rathna Nayakar & Sons, Thirumagal Achagam, Chennai.
Mohammad Azam Khan et al., "Key Attributes of TKDL", Ikseer Azam, vol. IV, 1872, Matba Nizami, Kanpur.
Jacobson et al., "Pharmacokinetics, Safety, and Antiviral Effects of Hypericin, a Derivative of St. John's Wort Plant, in Patients with Chronic Hepatitis C Virus Infection", Antimicrob. Agents Chemother., 2001, 45(2):517-524.
Japanese Office Action issued on Jan. 31, 2012 for Japanese Patent Application No. JP 2008-517271.
Cambazard, Traitements symptomatiques locaux et généraux de la varicelle et du zona (en dehors des antalgiques et des antiviraux., Médecine et maladies infectieuses, Conférence de Consensus en Thérapeutique Anti-infectieuse No. 11, Lyon, France (Mar. 25, 1998) 1998, vol. 28, No. 11 (137 p.), pp. 810-815 (7 pages total with English Summary).

\* cited by examiner

COMPOSITION FOR TREATING SKIN LESIONS

TECHNICAL FIELD

The present invention relates to a composition for the treatment of skin lesions and use of the composition. In particular, the invention relates to compositions for treatment of skin lesions associated with viral infections, such as Herpes simplex.

BACKGROUND ART

Herpes is a sexually transmitted disease (STD) caused by the herpes simplex virus (HSV). There are two types of HSV; Herpes Simplex 1 (HSV1) and Herpes Simplex 2 (HSV2).

HSV1 or mouth herpes is commonly in the form of cold sores on and around the mouth. HSV2 or genital herpes is a much more intense strain commonly found on the genitals. However both types can be found on the mouth or genital areas. It is possible to be infected by both HSV1 and HSV2. Being infected by one particular strain does not make you immune to another.

Recurrent outbreaks of the Herpes virus generally follow a staged progression. The stages are easily identifiable and include prodrome, vesicles, ulceration, crust and healing. Prodrome is generally a short period of tingling, itching, numbness or burning with no visible sign of an outbreak. Vesicles are the formation of one or more fluid-filled blisters, often in a cluster and usually surrounded by sore, red skin. The ulceration stage is when the blisters open to form painful ulcers or open sores. At the edge of the sore, a soft or hard yellow crust begins to appear. Ulcers and painful, sore, red skin persist through this stage. At the crust stage, weeping sores or ulcers become completely covered by a crust or scab. No ulcers or blisters are present. The healing process is manifested by disappearance of the crust, swelling, pain and itching. Skin eruptions due to viral infection, especially Herpes viruses, generally have a normal infective course that lasts from 10 to 60 days depending on the exact causative species and anatomical location of the infection.

After the initial outbreak, the virus usually lies dormant in the skin or in nerve tissue (latent state) until something triggers another eruption or site infection. When the virus reactivates, it characteristically causes a sore at the site where it first entered the body. Often the trigger is unknown, but in some people overexposure to sunlight, fever, physical or emotional stress, hormonal changes such as pregnancy or menstruation, or certain foods and drugs seem to reactivate the virus.

Genital herpes on the other hand is generally considered to be sexually transmitted. An estimated 40 million people of the world population have genital herpes which makes it a chronic viral infection. About 500,000 people get new symptomatic herpes each year and there are even more people without symptoms. It has been estimated that about 20% of the world population have genital herpes and 90% have oral herpes (cold sores).

To date, there is neither a vaccine to prevent the Herpes infection, nor any way to eliminate the virus from the body. The fact that the herpes virus retreats into the nervous system makes it extremely difficult to eliminate completely.

Previous treatments for herpes virus infections have included the topical application of 5% by weight of acyclovir (Zovirax®), oral administration of valacyclovir HCI (Valtrex®) and laser treatments such as Lectroject®. Each of these treatments is expensive to the patient and the effectiveness is quite slow and often painful. Side effects such as headache and nausea are not uncommon when using repeated applications of acyclovir, whilst the Lectroject® laser method of treating herpes increases the possibility of scar tissue formation.

Accordingly, there remains a need for an effective treatment of skin lesions, and in particular, skin lesions associated with viral infections such as Herpes. Most herpes medications act to "suppress" the virus inside the body in order to reduce outbreaks. In contrast, the present inventors have developed a composition which works by substantially eliminating the virus on direct contact at the outbreak site which accelerates the recovery time of the viral outbreaks and reduces the inconvenience and embarrassment of the condition.

SUMMARY OF INVENTION

The present invention generally provides topical preparations and methods for treatment of skin and mucosal membrane lesions associated with microbial infections such as Herpes simplex.

In a first aspect, the present invention provides a composition for topical treatment of skin and mucosal membrane lesions comprising a synergistic combination of:
 a copper compound; and
hypericum perforatum extract.

The composition may further comprise a skin protectant.

The composition may further comprise a preservative. Preferably, the preservative is Germall Plus (Diazolidinyl Urea and Iodopropyynyl Butylcarbamate from ISP Sutton Laboratories).

Preferably, the composition comprises:
(a) about 5-9% (w/w) copper compound;
(b) about 0.05 to 0.15% (w/w) hypericum perforatum extract;
(c) about 1 to 5% (w/w) a skin protectant;
(d) optionally about 0.1 to 0.3% (w/w) preservative; and (e) balance water.

Preferably the copper compound is in the form of copper sulphate, copper chloride or copper salicylate. More preferably, the copper compound is in the form of copper sulphate, and more preferably copper sulphate pentahydrate.

Preferably, the copper compound is provided as copper sulphate at about 5-9% (w/w), more preferably as copper sulphate pentahydrate.

Typically, the copper compound provides copper ions at a concentration of about 1-5% (w/w).

Preferably, the copper sulphate is at a concentration of about 5% by weight. More preferably, the copper sulphate pentahydrate is at a concentration of about 7.8% by weight.

Hypericum perforatum is plant extract (flower extract) and can be obtained or prepared by means of solvent (ethanol) extraction. Preferably, the hypericum perforatum is at a concentration of about 0.1% by weight.

The composition may further comprise aloe vera. Aloe vera is obtained from the Aloe barbadenisis plant which is a cactus-like plant belonging to the Lilly family and can be obtained or prepared by means of solvent (ethanol) extraction. Preferably, the aloe vera is at a concentration of about 1.0% by weight.

In one embodiment, the composition may further comprise sodium ascorbate. Preferably the sodium ascorbate is at a concentration of about 3-10% (w/w). In another embodiment, the composition may further comprise hydrogen peroxide. Preferably, the hydrogen peroxide is at a concentration of about 3-10% (w/w).

Preferably, the skin protectant is selected from the group consisting of glycerin or sorbitol. More preferably, the skin protectant is glycerin. The skin protectant is preferably used at a concentration of about 5.0% by weight.

Preferably, the water is at a concentration of about 60% to 85% by weight.

Preferably, the composition is in a form selected from a cream, lotion, emollient, gel, or emulsion.

In a second aspect, the present invention provides a method of treating or preventing skin lesions comprising applying to the lesion a therapeutically effective amount of a composition according to the first aspect of the present invention.

In a third aspect, the present invention provides use of a composition according to the first aspect of the present invention for the manufacture of a medicament for the treatment or prevention of viral associated skin or mucosal membrane lesions.

Preferably, the composition is applied once per viral infection.

Preferably, the composition is applied to a visible and mature lesion.

In one preferred form, the lesions are located on or around the mouth area.

In another preferred form, the lesions are located on or around the genital region of a subject.

Preferably, the lesions are associated with a skin infection. More preferably, the skin infection may be associated with a bacterial, fungal or viral infection.

Preferably the lesions are associated with a viral infection. More preferably, the viral infection is selected from Herpes Simplex virus, Herpes Zoster virus, Polio virus, Shingles-associated viruses, Varicella Zoster virus, Chicken pox-associated viruses or Human Immunodeficiency virus. Preferably, the virus is Herpes Simplex virus.

Preferably, the lesions are associated with a fungal infection. More preferably, the fungal infection is tinea.

The carriers, excipients and/or diluents utilised should be acceptable for human or veterinary applications. Such carriers, excipients and/or diluents are well-known to those skilled in the art. Carriers and/or diluents suitable for use include any and all solvents, dispersion media, aqueous solutions, coatings, antibacterial and antifungal agents, isotonic and absorption delaying agents, and the like. Except insofar as any conventional media or agent is incompatible with the active ingredient, use thereof in the composition is contemplated. Supplementary active ingredients can also be incorporated into the compositions.

In a fourth aspect, the present invention provides a process of producing a composition for the treatment of viral associated skin and mucosal membrane lesions, the process comprising:

forming a copper solution from a copper compound;
optionally adding glycerin to the copper solution;
adding hypericum perforatum to the copper solution;
bringing the solution to a desired concentration using water;
optionally adding a preservative; and optionally
filtering to remove any sediment.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of the invention disclosed in this application.

In order that the present invention may be more clearly understood, preferred forms will be described with reference to the following examples.

MODE(S) FOR CARRYING OUT THE INVENTION

Previous topical medications have used high concentrations of copper sulphate, some as high as 10% by weight. High concentrations of copper have been found to cause blood poisoning which can be potentially fatal. In contrast, the present inventors have surprisingly shown that a copper compound used at a concentration of 5-9% by weight in combination with 0.05 to 0.15% by weight of hypericum perforatum extract provides a synergistic antiviral effect in the treatment of skin lesions. Use of a lower concentration of copper results in the composition being safe, providing an effective dose to be used topically, even on open wounds. Prior art uses indicate that it is necessary to use high concentrations of copper sulphate to provide adequate anti-viral activity.

The present inventors have found that the combination of copper compound and hypericum perforatum extract according to the present invention is significantly more effective and has an antimicrobial affect at lower concentrations than the use of the copper compound or hypericum perforatum extract alone.

It has now been found and is the subject of the present invention that a composition comprising a synergistic combination of copper, preferably in the form of copper sulphate pentahydrate and a herbal antiviral agent such as hypericum perforatum is effective in dramatically reducing the healing time of viruses such as Herpes lesions, stopping the normal progression of the viral outbreak from the stage at which the initial outbreak occurred, and also in reducing further recurrences of the virus.

The composition of the present invention is a copper-based solution with copper as the active trace metal in an aqueous herbal base.

The present invention relates to the use of chemically supplemented compositions for the treatment of viral associated skin and mucosal membrane lesions. The present inventors have found that a combination of copper, preferably in the form of copper sulphate and the herbal antiviral agent hypericum perforatum extract, provides a synergistic antiviral effect in the treatment of skin lesions. In this aspect, there is provided a composition and method for treating viral associated skin and/or oral mucosa lesions. The method of which comprises administration to the patient an effective amount of a composition preferably comprising copper sulphate and hypericum perforatum.

The compositions of the present invention are those recognised in the pharmaceutical arts as being suitable for topical application and include, without intended limitation, creams, lotions, liquid emulsions, gels, aqueous solutions and the like. The present compositions preferably include copper sulphate pentahydrate in from about 5 to 9, preferably 7.8% by weight or copper ion from about 1 to 5%, (equivalent to about 3 to 7% copper sulphate), preferably 5% by weight, glycerin in from about 5% by weight and hypericum perforatum extract in from about 0.05 to 0.15%, preferably about 0.1% by weight. The careful selection of the components of the present composition has provided an optimal antiviral effect that has produced unexpectedly enhanced results. In addition to the enhanced therapeutic effect, the subject composition is also advantageous in that it is safe and has no known side-effects, unlike many previous copper-based preparations. The composition can also be safely used for veterinary purposes.

The skin protectant forms a barrier over the skin surface to protect against irritation due to touching, rubbing etc. The skin protectant also provides a protective barrier over the lesion, preventing loss of the active ingredient to the action of saliva. In a preferred embodiment, the skin protectant is in the form of glycerin.

In addition to the foregoing ingredients, the composition of the present invention may contain other ingredients such as are recognised by those skilled in the pharmaceutical industry as being typically present in such formulations. These include, without limitation, one or more preservatives, osmotic regulators, thickeners, flavours, fragrances, emollients, humectants, colorants, pigments and the like. It would be clear to the skilled addressee that the compounding of the composition of the present invention will be carried out utilising some or all of these ingredients depending on the area of application and intended use. For example, for a preparation intended for application in or around the mouth, it may be necessary to add flavours to mask the taste of the essential ingredients.

Although best long term results are achieved by applying the composition to a visible and mature lesion, patients have reported great success in preventing outbreaks by applying the composition in the early stages. This can include applying the composition topically to the affected area as the first sign of symptoms such as itching, tingling, redness or inflammation.

EXAMPLES

Example 1

An aqueous solution was prepared from formula 1 given below.

Formula 1

| Components | Typical Amount |
| --- | --- |
| Assay as copper sulphate pentahydrate ($CuSO_4 \cdot 5H_2O$) | 7.80% w/w max |
| (Assay equivalent copper sulphate anhydrous ($CuSO_4$)) | 5.0% w/w max |
| Glycerin (Glycerol) | 5.0% w/w max |
| Hypericum perforatum | 0.1% v/v max |
| Germall Plus (preservative) | 0.3% v/v max |
| Water Purified | Balance |

Formula 2

| Components | Typical Amount |
| --- | --- |
| Assay as copper sulphate | 9% w/w max |
| Glycerin (Glycerol) | 5% w/w max |
| Hypericum perforatum | 0.15% v/v max |
| Germall Plus (preservative) | 0.3% v/v max |
| Water Purified | Balance |

Formula 3

| Components | Typical Amount |
| --- | --- |
| Assay as copper sulphate | 5% w/w max |
| Glycerin (Glycerol) | 1% w/w max |
| Hypericum perforatum | 0.05% v/v max |
| Germall Plus (preservative) | 0.1% v/v max |
| Water Purified | Balance |

Formula 4

| Components | Typical Amount |
| --- | --- |
| Assay as copper chloride | 9% w/w max |
| Glycerin (Glycerol) | 3.0% w/w max |
| Hypericum perforatum | 0.2% v/v max |
| Germall Plus (preservative) | 0.2% v/v max |
| Water Purified | Balance |

Formula 5

| Components | Typical Amount |
| --- | --- |
| Assay as copper chloride | 9% w/w max |
| Glycerin (Glycerol) | 3.0% w/w max |
| Hypericum perforatum | 0.2% v/v max |
| Germall Plus (preservative) | 0.2% v/v max |
| Water Purified | Balance |

Formula 6

| Components | Typical Amount |
| --- | --- |
| Assay as copper salicylate | 9% w/w max |
| Glycerin (Glycerol) | 3.0% w/w max |
| Hypericum perforatum | 0.2% v/v max |
| Germall Plus (preservative) | 0.2% v/v max |
| Water Purified | Balance |

The solution was prepared by filling a suitable vessel with about 60% distilled water. Copper compound was added to the water with continuous stirring. Mixing of the solution continued for 10 minutes or until the copper was fully dissolved. Glycerin was added to the solution and mixed for a few minutes. Hypericum perforatum was gradually added to the solution with continuous mixing. The solution was then brought to final weight by the slow addition of the required amount, of water with continuous blending for about 10 minutes. Preservative German Plus was added to the solution and the solution was then allowed to stand for 12 to 15 hours to stabilise. The solution was then filtered to remove the sediment and packaged.

Example 2

Treatment of Herpes Simplex Patients with the Composition

The solution prepared in Example 1 was tested for its effectiveness against Herpes virus. In order to determine the effectiveness of the composition in reducing the healing time of the Herpes outbreak and/or reducing the recurrence of the outbreaks, 51 patients were observed.

Of the 51 patients treated with the composition, 34 suffered from mouth lesions associated with Herpes Simplex virus 1 and 19 suffered from genital lesions associated with Herpes Simplex virus 2 (2 patients suffered from both mouth and genital lesions). Following topical application of the composition to the area of the viral-associated lesion, 38 of the 51 patients reported a dramatic reduction in the healing time of the lesion (with scab formation occurring within 24 hours) and 47 of the 51 patients reported a reduced recurrence of the viral outbreaks. All patients reported a substantial reduction in pain and discomfort associated with the lesions following application of the composition.

Example 3

Prospective, Comparative Study to Evaluate the Safety, Tolerability and Efficacy of the Composition in Patients Suffering from Herpes Simplex Infection (HSV1 and HSV2)

The trial enrolled 150 herpes simplex patients (HSV 1 & HSV 2) who have active lesions on external genitalia and skin, between the ages of 18 and 55 years. Subjects were randomized into two groups (A and B). Subjects in Group A topically applied a composition as defined in Example 1, transferring 2-4 drops (depending upon the affected area) to a wet cotton swab (enough to saturate it) on the affected part only once at clinic.

Subjects in Group B topically applied 0.5-1.5 grams of the comparator article (Acyclovir 5% cream) twice daily (once in the morning and once at night) to cover the affected area for 7 days.

The patients in Group A presented for efficacy & safety assessments on Day 2, Day 3, Day 8 and Day 14. Group B patients presented on Day 3 and Day 8 for efficacy evaluation and on Day 14 for follow up. Patients also recorded his/her assessment of symptoms on a patient diary from Day 1 to Day 14.

Safety were evaluated by adverse event reports throughout the study. Hematology and clinical chemistry labs, urinalysis, and physical exam of basic systems were obtained at initial screening and Day 14 (end of study) visits. Treatment was be initiated on Day 1, pending the results of laboratory investigations. The patient was withdrawn immediately from the study if the results show abnormal values in laboratory investigation reports.

Efficacy endpoint assessments shall be completed to determine time to ≥50% crusting/scabbing or healed ulcer within 48 hours. Cutaneous assessments include disappearance of Erythema, Crust/Scab formation in ulcers, disappearance of pain and disappearance of itching and burning sensation.

Cutaneous efficacy assessments shall be performed at each visit on Day 2, Day 3 and Day 8 in Group A while in Group. B it were performed on Day 3 and Day 8 or until 100% crusting was observed.

Local cutaneous tolerability shall be evaluated with assessments of erythema, induration and stinging sensation on Day 1, Day 2, Day 3 and Day 8 in Group A and on Day 3 and Day 8 in Group B or until 100% crusting is observed.

The foregoing case studies demonstrated the enhanced effectiveness of the composition in accordance with the present invention in the treatment of skin and mucosal membrane lesions caused by Herpes infections.

It will be appreciated by persons skilled in the art that numerous variations and/or modifications may be made to the invention as shown in the specific examples without departing from the spirit or scope of the invention as broadly described. The present examples are, therefore, to be considered in all respects as illustrative and not restrictive.

The invention claimed is:

1. A composition for topical treatment of microbial associated skin and/or mucosal membrane lesions consisting of:
    water;
    a copper compound at a concentration of 5% to 9% (w/w) or in an amount sufficient to provide copper ion concentration of 1% to 5% (w/w);
    an amount of hypericum perforatum extract at a concentration of 0.05% to 0.15% (v/v); and
    optionally a preservative; and
    optionally a skin protectant; and
    optionally aloe vera at a concentration of 1.0% (w/w); and
    optionally sodium ascorbate at a concentration of 3% to 10% (w/w); and
    optionally hydrogen peroxide at a concentration of 3% to 10% (w/w).

2. The composition according to claim 1, wherein the copper compound is copper sulphate, copper chloride or copper salicylate.

3. The composition according to claim 1, wherein the copper compound is copper sulphate.

4. The composition according to claim 1, wherein the copper compound is copper sulphate pentahydrate or copper sulphate anhydrous.

5. The composition according to claim 1, wherein the copper compound is copper sulphate and is present in said composition at a concentration of 7.8% (w/w).

6. The composition according to claim 1, wherein the preservative is present in the composition.

7. The composition according to claim 6, wherein the preservative is Diazolidinyl Urea and lodopropyynyl Butylcarbamate.

8. The composition according to claim 6, wherein the preservative is at a concentration of 0.1 to 0.3% (w/w).

9. The composition according to claim 1, wherein the skin protectant is present in the composition.

10. The composition according to claim 9, wherein the skin protectant is at a concentration of 1 to 5% (w/w).

11. The composition according to claim 9, wherein the skin protectant is glycerin.

12. The composition according to claim 1, wherein the aloe vera is present in the composition at a concentration of 1.0% (w/w).

13. The composition according to claim 1, wherein the sodium ascorbate is present in the composition at a concentration of 3% to 10% (w/w).

14. The composition according to claim 1, wherein the hydrogen peroxide is present in the composition at a concentration of 3% to 10% (w/w).

15. The composition according to claim 1 in the form of a cream, lotion, emollient, gel or emulsion.

16. A method of topically treating viral associated skin and/or mucosal membrane lesions comprising applying to the lesion a therapeutically effective amount of a composition consisting of:
    water;
    a copper compound at a concentration of 5% to 9% (w/w) or in an amount sufficient to provide copper ion concentration of 1% to 5% (w/w);
    an amount of hypericum perforatum extract at a concentration of 0.05% to 0.15% (v/v); and
    optionally a preservative; and
    optionally a skin protectant; and
    optionally aloe vera at a concentration of 1.0% (w/w); and
    optionally sodium ascorbate at a concentration of 3% to 10% (w/w); and
    optionally hydrogen peroxide at a concentration of 3% to 10% (w/w).

17. The method according to claim 16, wherein the skin and/or mucosal membrane lesions are caused by an infection with a virus selected from the group consisting of Herpes Simplex virus, Herpes Zoster virus, Polio virus, Shingles-associated viruses, Varicella Zoster virus, Chicken pox-associated viruses and Human Immunodeficiency virus.

18. The method according to claim 16, wherein the skin and/or mucosal membrane lesions are caused by an infection caused by Herpes Simplex virus.

19. The method according to claim 16, wherein the preservative is present in the composition.

20. The method according to claim 16, wherein the skin protectant is present in the composition.

21. The method according to claim 16, wherein the aloe vera is present in the composition.

22. The method according to claim 16, wherein the sodium ascorbate is present in the composition.

23. The method according to claim 16, wherein the hydrogen peroxide is present in the composition.

24. A process of producing the composition of claim 11, said process comprising:
 forming a copper solution from a copper compound at a concentration of 5% to 9% (w/w) or in an amount sufficient to provide copper ion concentration of 1% to 5% (w/w);
 adding glycerin to the copper solution;
 adding hypericum perforatum to the copper solution;
 bringing the solution to a desired concentration using water;
 optionally adding a preservative; and
 optionally filtering to remove any sediment.

\* \* \* \* \*